US00PP35858P2

(12) United States Plant Patent
Loonen

(10) Patent No.: US PP35,858 P2
(45) Date of Patent: Jun. 4, 2024

(54) ***GAILLARDIA* PLANT NAMED 'FLOGB0060'**

(50) Latin Name: *Gaillardia aristata*
Varietal Denomination: FLOGB0060

(71) Applicant: Florensis B.V., Hendrik-Ido-Ambacht (NL)

(72) Inventor: Rik Petrus Louis Loonen, Oosteind (NL)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 18/373,375

(22) Filed: Sep. 27, 2023

Related U.S. Application Data

(60) Provisional application No. 63/446,048, filed on Feb. 16, 2023.

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
CPC ..... A01H 6/14; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Gaillardia* plant named 'FLOGB0060', characterized by its single-type, medium red-colored inflorescences with yellow-colored tips, medium green-colored foliage, and moderately vigorous, compact-mounded growth habit, is disclosed.

1 Drawing Sheet

Latin name of genus and species of plant claimed: *Gaillardia aristata.*

Variety denomination: 'FLOGB0060'.

BACKGROUND OF THE INVENTION

The present invention relates to a new and distinct cultivar of *Gaillardia* plant botanically known as *Gaillardia aristata* and hereinafter referred to by the cultivar name 'FLOGB0060'.

The new cultivar originated in a controlled breeding program in Hendrik-Ido-Ambacht, the Netherlands during August 2017. The objective of the breeding program was the development of *Gaillardia* cultivars having large inflorescences, with attractive flower coloration, substantially continuous blooming from early summer through fall, and a multi-branched, compact-mounded growth habit suitable for bedding and pot plants use.

The new *Gaillardia* cultivar is the result of cross-pollination. The female (seed) parent of the new cultivar is Gallo Dark Bicolor 'KIEGALDAB', U.S. Plant Pat. No. 20,718, characterized by its single-type, dark burgundy-colored inflorescences with yellow-colored tips, medium green-colored foliage, and moderately vigorous, compact-mounded growth habit. The male (pollen) parent of the new cultivar is 'Sunset Flash', U.S. Plant Pat. No. 26,945, characterized by its semi-double type, medium orange-red colored inflorescences with dark yellow-colored tips, medium gray-green colored foliage, and moderately vigorous, compact-mounded growth habit. The new cultivar was discovered and selected as a single flowering plant within the progeny of the above stated cross-pollination during July 2018 in a controlled environment in Hendrik-Ido-Ambacht, the Netherlands.

Asexual reproduction of the new cultivar by terminal stem cuttings since July 2018 in Hendrik-Ido-Ambacht, the Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'FLOGB0060' as a new and distinct cultivar of *Gaillardia* plant:

1. Single-type, medium red-colored inflorescences with yellow-colored tips;
2. Medium green-colored foliage; and
3. Moderately vigorous, compact-mounded growth habit.

Plants of the new cultivar differ from plants of the female parent primarily in having lighter red-colored inflorescences. Plants of the new cultivar differ from plants of the male parent primarily in having fewer ray florets per inflorescence and darker green colored foliage.

Of the many commercially available *Gaillardia* cultivars, the most similar in comparison to the new cultivar is the *Gaillardia* cultivar Barbican Yellow Red Ring 'GAIZ0007', U.S. Plant Pat. No. 29,529. However, in comparison, plants of the new cultivar differ from plants of 'GAIZ0007' in at least the following characteristics:

1. Plants of the new cultivar have larger diameter inflorescences than plants of 'GAIZ0007'; and
2. Plants of the new cultivar have shorter peduncles than plants of 'GAIZ0007'.

Plants of the new cultivar can also be compared to 'FLOGA0001', co-pending U.S. Plant patent application Ser. No. 18/373,372, and were shown to differ from plants of 'FLOGA0001' in at least the following characteristics:

1. Plants of the new cultivar are taller and wider than plants of 'FLOGA0001';
2. Plants of the new cultivar have larger diameter inflorescences than plants of 'FLOGA0001'; and
3. Plants of the new cultivar have smaller leaves than plants of 'FLOGA0001'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'FLOGB0060'. The plants were approximately 4.5 months old and grown in 1.72-gallon containers for approximately 2.5 months in an outdoor nursery environment in West Chicago, Illinois. Plants were given two pinches prior to transplant.

DETAILED BOTANICAL DESCRIPTION

Figure 1:
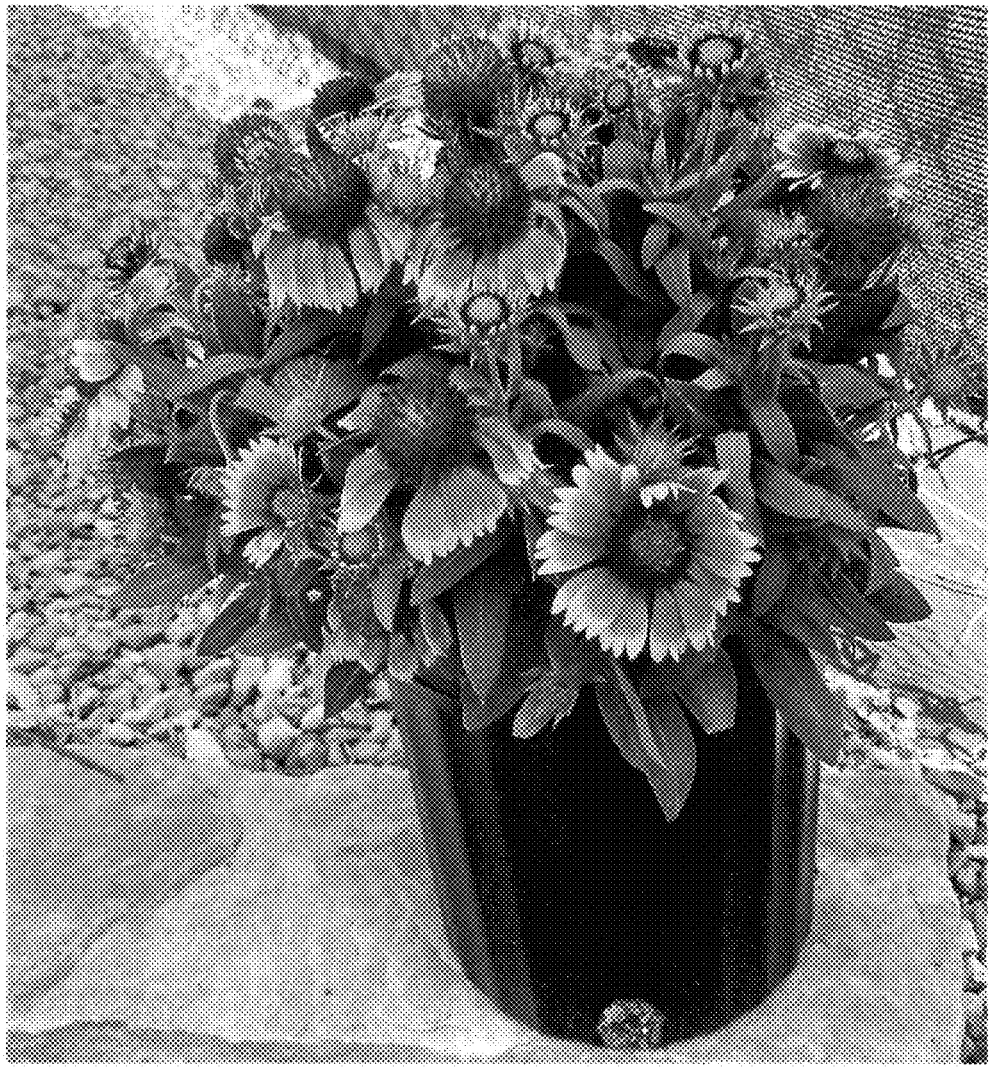
FIG. 1 illustrates a side view of the overall growth and flowering habit of 'FLOGB0060'.
Figure 2:
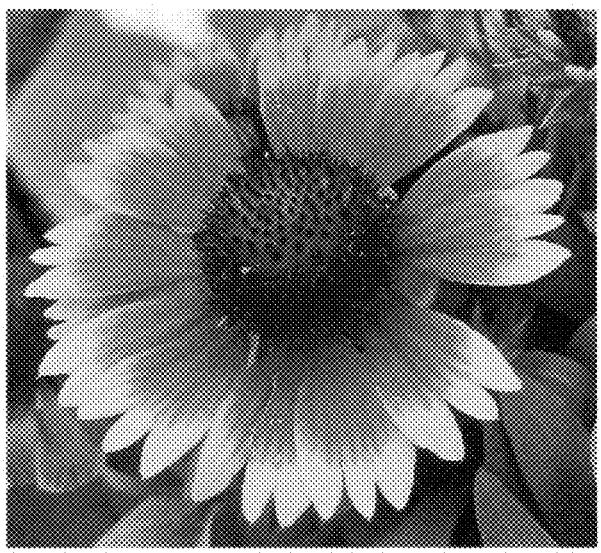
FIG. 2 illustrates a close-up view of an inflorescence of 'FLOGB0060'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2023 under natural light conditions in Naperville, Illinois.

The following descriptions and measurements describe approximately 4.5-month old plants produced from cuttings from stock plants and grown under conditions comparable to those used in commercial practice. Approximately 8 weeks after sticking, plants were transplanted in 1.72-gallon containers utilizing a soilless growth medium. Plants were then transferred to an outdoor nursery environment in West Chicago, Illinois and grown for approximately 2.5 months. Prior to transferring outdoors, plants were grown in a polycarbonate greenhouse in West Chicago, Illinois. Plants were given two pinches prior to transplant. Greenhouse temperatures were maintained at approximately 70° F. to 75° F. (21.1° C. to 23.9° C.) during the day and approximately 60° F. to 65° F. (15.6° C. to 18.3° C.) during the night. Measurements and numerical values represent averages of typical plants.

Botanical classification: *Gaillardia aristata* 'FLOGB0060'.

Parentage:

*Female parent*.—Gallo Dark Bicolor 'KIEGALDAB', U.S. Plant Pat. No. 20,718.

*Male parent*.—'Sunset Flash', U.S. Plant Pat. No. 26,945.

Propagation:

*Type cutting*.—Terminal stem.

*Time to initiate roots*.—Approximately 2 weeks.

*Time to produce a rooted cutting*.—Approximately 4 weeks.

*Root description*.—Fibrous, fine to medium thickness.

Plant description:

*Commercial crop time*.—Approximately 8 to 10 weeks from a rooted cutting to finish in a one-gallon container.

*Growth habit and general appearance*.—Herbaceous perennial, moderately vigorous, compact-mounded growth habit.

*Hardiness*.—USDA Zone 5a (−20° F. to −15° F./−28.9° C. to −26° C.).

*Size*.—Height from soil level to top of plant plane: Approximately 24.0 cm. Width: Approximately 41.0 cm.

*Branching habit*.—Freely branching, pinching enhances basal branching. Quantity of main branches per plant: Approximately 12.

*Branch*.—Strength: Strong. Length: Approximately 11.0 cm. Diameter: Approximately 4.0 mm to 5.0 mm. Length of central internode: Approximately 2.0 cm. Texture: Densely pubescent. Color of young and mature stems: 146D.

Foliage description:

*General description*.—Quantity of leaves per main branch: Approximately 5. Fragrance: None detected. Form: Simple. Arrangement: Alternate.

*Leaves*.—Aspect: Acute angle to stem. Shape: Lanceolate. Margin: Entire. Apex: Acute. Base: Sessile. Venation pattern: Pinnate. Length of mature leaf: Approximately 6.2 cm. Width of mature leaf: 1.3 cm. Texture of upper and lower surfaces: Densely pubescent. Color of upper surface of young and mature foliage: NN137C with midvein of 146D. Color of lower surface of young and mature foliage: NN137D with midvein of 146D.

Flowering description:

*Flowering habit*.—'FLOGB0060' is freely flowering under outdoor growing conditions with substantially continuous blooming from early summer through autumn.

*Lastingness of individual inflorescence on the plant*.—Approximately 7 to 10 days.

Inflorescence description:

*General description*.—Type: Semi-double type composite, actinomorphic. Not persistent. Shape: Round. Aspect: Erect. Arrangement: Terminal capitulum, positioned primarily above the foliage. Quantity per plant: Approximately 19. Diameter: Approximately 8.0 cm. Depth: Approximately 2.2 cm. Fragrance: Faint, sweet.

*Peduncle*.—Strength: Moderately strong, flexible. Aspect: Erect. Length: Approximately 8.0 cm. Diameter: Approximately 3.0 mm. Texture: Densely pubescent. Color: 146D.

*Bud*.—Rate of opening: Generally takes 5 to 7 days for bud to progress from first color to fully open inflorescence. Quantity per plant: Approximately 32.

*Bud just before opening*.—Shape: Oblate. Width: Approximately 1.2 cm. Depth: Approximately 7.0 mm. Color: 145A.

*Ray florets*.—Quantity per inflorescence: Approximately 17. Arrangement: In one to two whorls, imbricate. Aspect: Horizontal to slightly upright. Shape: Spatulate. Margin: Entire. Apex: Notched.

Base: Attenuate. Length: Approximately 3.4 cm. Width: Approximately 1.6 cm. Texture of upper surface: Glabrous. Texture of lower surface: Moderately pubescent. Color of upper surface when first open: N34A with tips of 13A. Color of lower surface when first and fully open: 13C with an underlay of N34A to N34B. Color of upper surface when fully open: 34A and N34A with tips of 13A, fading with age to 34C and N34C with tips of between 13A and 13B.

*Disc florets*.—Quantity per inflorescence: Approximately 125. Arrangement: Massed in center of inflorescence. Shape: Tubular with flared tips, pappus at base of tube NN155D in color and approximately 7.0 mm in length. Margin: Entire. Apex: Five acute tips. Base: Fused. Length: Approximately 1.5 cm. Diameter at apex: Approximately 4.0 mm. Diameter at base: Approximately 1.0 mm. Texture of outer surface: Densely pubescent, colored 187A to 187B at tips. Texture of inner surface: Glabrous. Color of outer and inner surfaces when first and fully open: 145A with 187A at tips and NN155D at base.

*Disc*.—Diameter: Approximately 3.0 cm. Depth: Approximately 1.7 cm.

*Receptacle*.—Shape: Dome. Height: Approximately 3.0 mm. Diameter at base: Approximately 5.0 mm. Color: 155D.

*Phyllaries*.—Quantity per inflorescence Approximately 24. Arrangement: In multiple whorls. imbricate. Shape: Lanceolate. Margin: Entire. Apex: Acute. Base: Truncate. Length of outermost: Approximately 1.7 cm. Width of outermost: Approximately 5.0 mm. Length of innermost: Approximately 1.1 cm. Width of innermost: Approximately 2.0 mm. Texture of upper and lower surfaces: Densely pubescent. Color of upper and lower surfaces: NN137D.

*Reproductive organs*.—Androecium: Present on disc florets only. Stamen quantity: 5. Stamen length: Approximately 7.0 mm. Anther shape: Oblong, connate around style. Anther length: Approximately 4.0 mm. Anther color: 17B with tips of 187A. Pollen amount: Abundant. Pollen color: 17A. Gynoecium: Present on disc florets only. Pistil quantity: 1 per floret. Pistil length: Approximately 1.5 cm. Stigma shape: Bifid. Stigma branch length: Approximately 6.0 mm. Stigma color: 187A. Style length: Approximately 6.0 mm. Style color: NN155D. Ovary length: Approximately 3.0 mm. Ovary color: NN155D.

Seed and fruit production: Neither seed nor fruit production has been observed.

Disease and pest resistance: Resistance to pathogens and pests common to *Gaillardia* has not been observed.

What is claimed is:

1. A new and distinct cultivar of *Gaillardia* plant named 'FLOGB0060', substantially as herein illustrated and described.

* * * * *